United States Patent [19]

Consadori et al.

[11] Patent Number: 5,055,270

[45] Date of Patent: Oct. 8, 1991

[54] GAS SENSOR

[75] Inventors: Franco Consadori; Richard Slamka, both of Vancouver; Konrad Colbow, West Vancouver, all of Canada

[73] Assignee: Halitec Industries Corp., Vancouver, Canada

[21] Appl. No.: 439,982

[22] Filed: Nov. 21, 1989

[30] Foreign Application Priority Data

Nov. 23, 1988 [CA] Canada .................................. 583969

[51] Int. Cl.$^5$ ........................ G01N 27/16; G05D 7/06
[52] U.S. Cl. ........................................ 422/98; 422/88; 422/110
[58] Field of Search ....................... 422/84, 88, 90, 98, 422/110, 116; 436/151, 178

[56] References Cited

U.S. PATENT DOCUMENTS 3,039,053 6/1962 Jacobson ................................ 422/98
3,858,434 6/1975 Hoppesch et al. ..................... 422/84

FOREIGN PATENT DOCUMENTS

87/07724 12/1987 World Int. Prop. O. ............ 422/84

Primary Examiner—Robert J. Warden
Assistant Examiner—Howard Hampel

[57] ABSTRACT

A gas sensing device has a sampling chamber for containing a gas to be sensed, with a gas sensing element with the chamber for providing an output signal which varies in response to the presence of the gas in the chamber. An orifice, or other restriction, permits gas flow between the interior and the exterior of the chamber and a pump, e.g. in the form of a heater, displaces a sample of the gas through the restriction into the interior of the chamber for sensing by the sensing element and subsequently displaces gas from the interior to the exterior of the chamber.

7 Claims, 6 Drawing Sheets

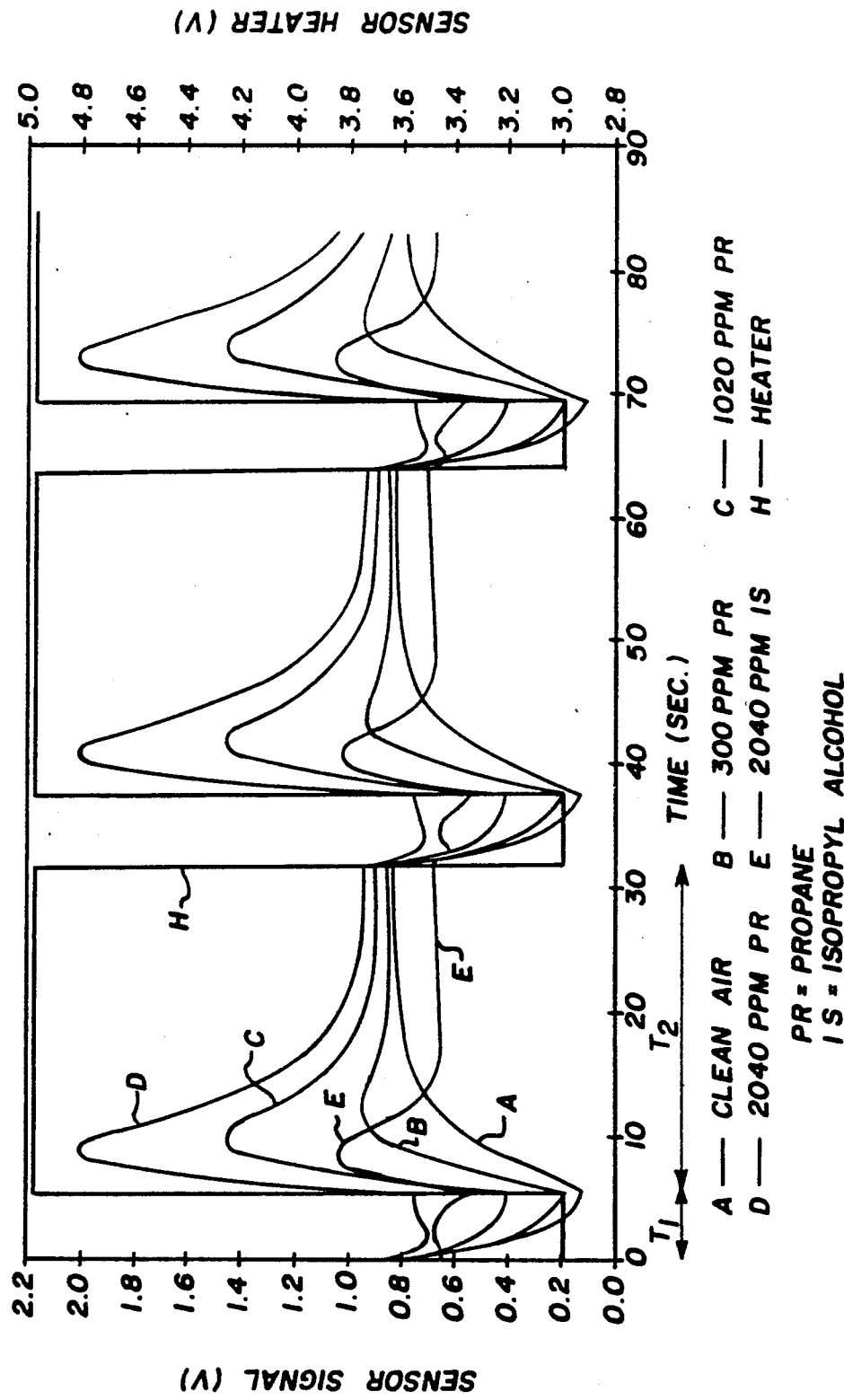

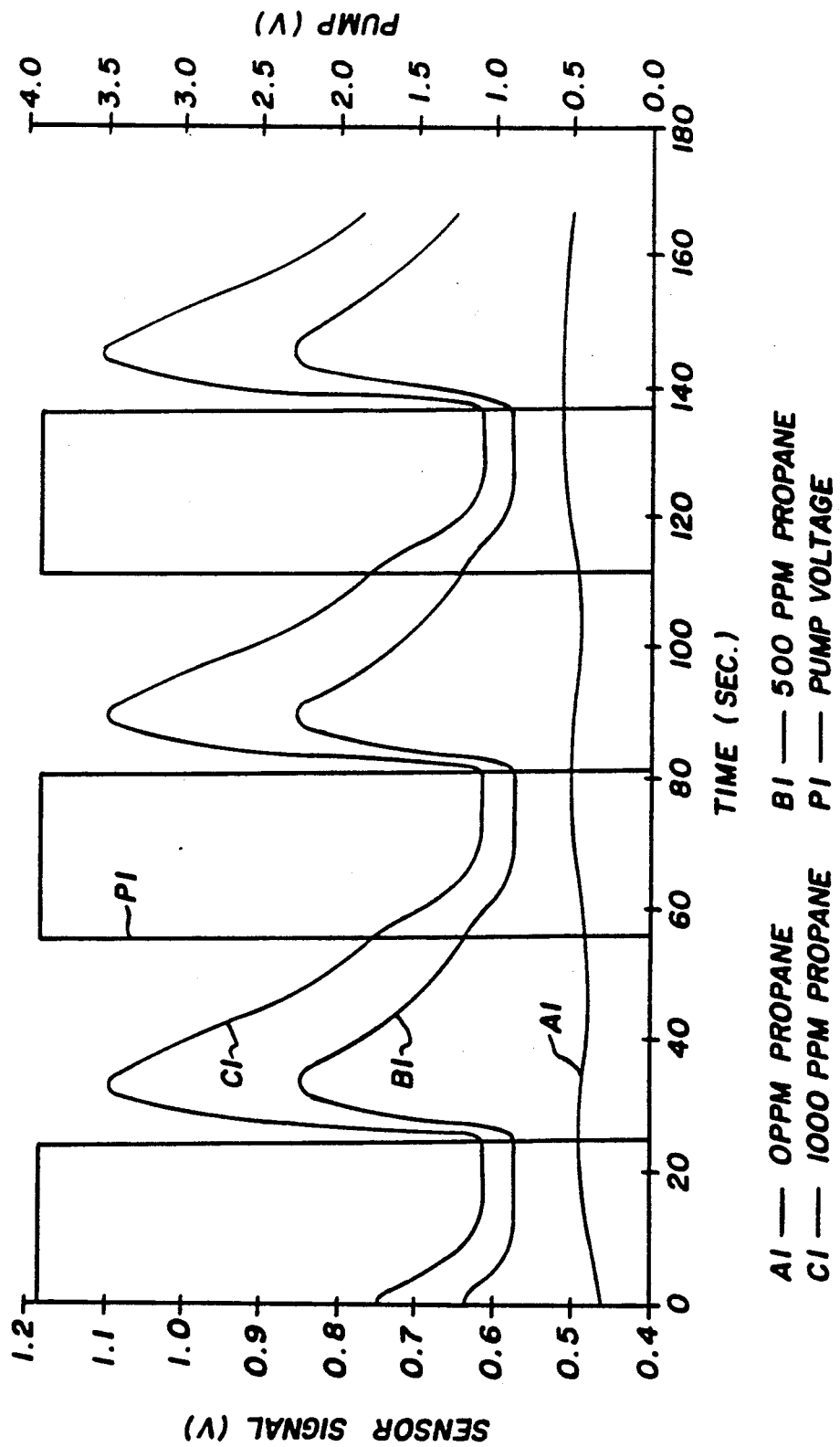

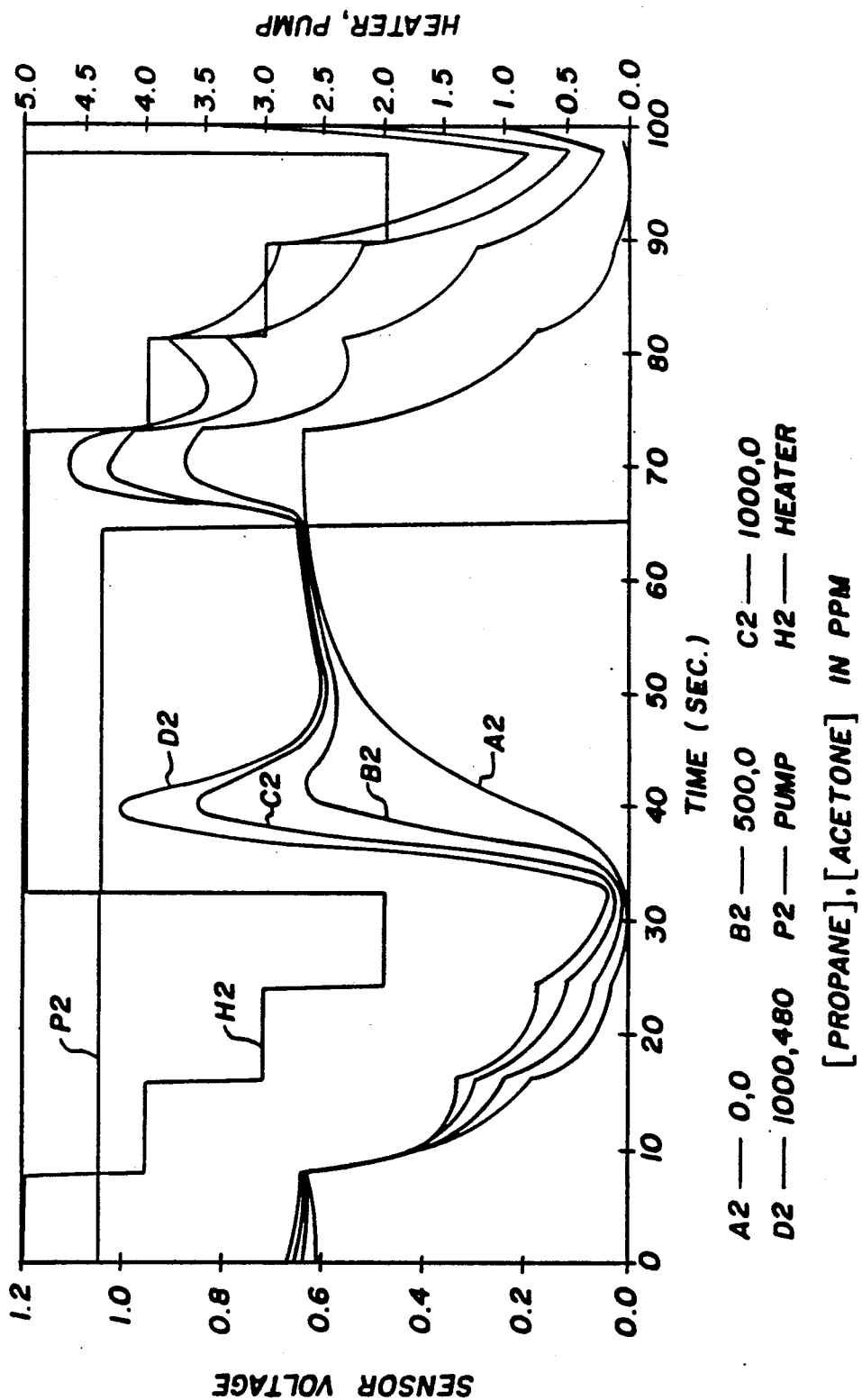

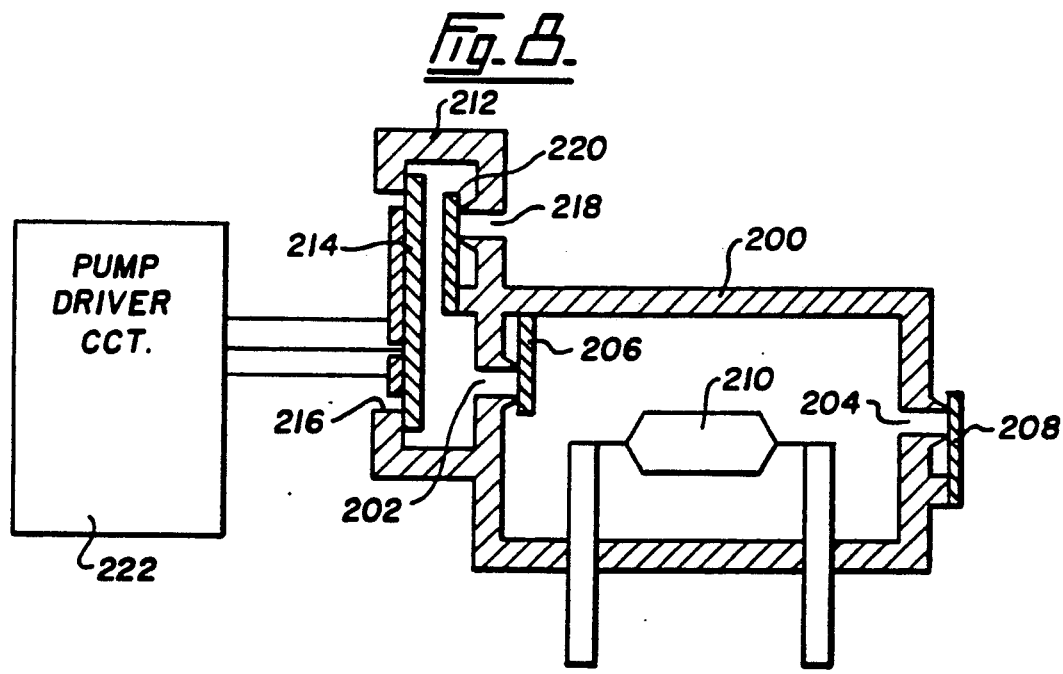
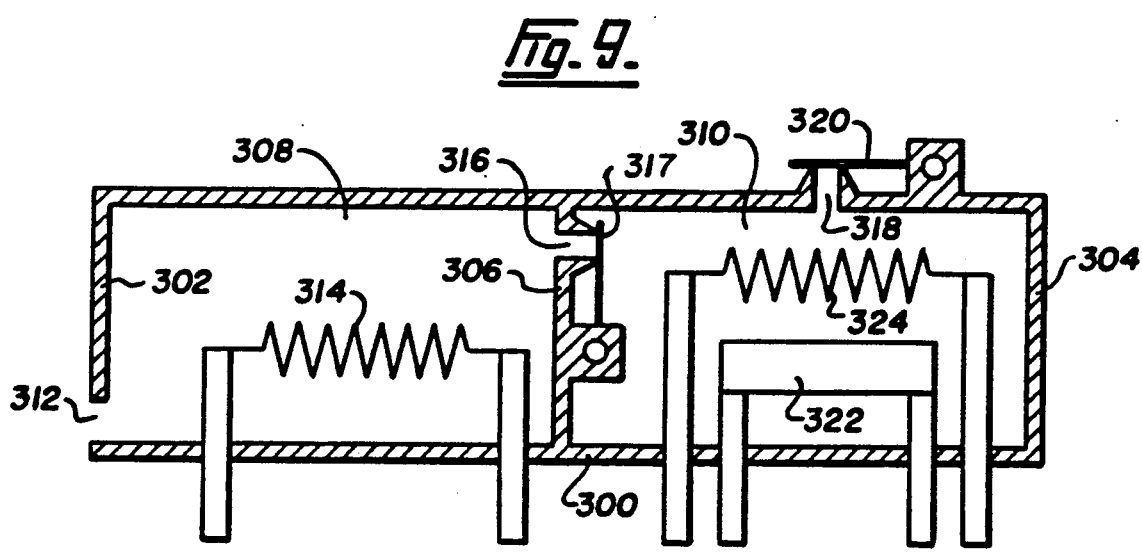

GAS SENSOR

FIELD OF THE INVENTION

The present invention relates to gas sensors and is useful in particular, but not exclusively, in association with metal oxide semiconductor gas sensors.

DESCRIPTION OF THE PRIOR ART

Various types of prior art gas sensors are known. These types include those in which a colour change is effected in response to a chemical reaction, optical interference gas sensors, infra red absorption gas sensors and catalytic gas sensors. However, the most widely used gas sensors are metal oxide semiconductor gas sensors, which are used, for example, for detecting and warning of explosive and toxic gases in domestic and industrial environments.

The metal oxide used in semiconductor gas sensors may be n-type, e.g. $SnO_2$, $ZnO$, $TiO_2$, $Fe_2O_3$ etc., or p-type, e.g. $CuO$, $NiO$, $CoO$ etc, although $SnO_2$ and $Y-Fe_2O_3$ are the metal oxides which are employed commercially.

A conventional prior art gas sensor comprises a porous semiconductor body of this metal oxide, which is capable of absorbing gas and which exhibits a consequential change in electrical conduction. The porous semiconductor body is formed of sintered metal oxide, and is mounted on a ceramic tube, a heating element being provided in the tube and a pair of electrodes being connected to the sintered material through which the electrical conductivity of the semiconductor body is detected.

This prior art gas sensor is mounted in a housing of resin or ceramic material provided with a flameproof cover of wire mesh. The semiconductor body, i.e. the sensor element, is exposed to the surrounding atmosphere through this mesh cover. Such a gas sensor is manufactured and sold, for example, by Figaro Engineering Inc., of Osaka, Japan.

The above-described prior art semiconductor gas sensors have a number of disadvantages. For example, since the sensing elements are exposed to the environmental conditions, the d.c. output signals of the sensors may have poor stability and accuracy due to sensitivity of the sensing element to humidity and temperature conditions. There may be instantaneous variations in the concentrations of the gases being sensed, due to unpredictably varying gas flow through the gas sensors. Also, the gas sensors cannot be used in environments that are potentially explosive since the heater elements of the gas sensors become hot in operation, i.e. are heated above 600 degrees Centigrade, and are separated from the environment only by the flame retarding mesh covers.

SUMMARY OF THE INVENTION

It is accordingly an object of the present invention to provide a novel and improved gas sensor in which the supply of the gas to be sensed by the sensing element can be effectively controlled.

According to the present invention, there is provided a gas sensing device comprising means defining a sampling chamber for containing a gas to be sensed by the sensing device, a gas sensing element within the chamber for providing an output signal which varies in response to the presence of the gas in the chamber, means for permitting restricted gas flow between the interior and the exterior of the chamber, and means for displacing a sample of the gas through the gas flow permitting means into the interior of the chamber for sensing by the sensing element and for subsequently displacing gas from the interior to the exterior of the chamber.

Although in the preferred embodiment of the invention the gas sensing element comprises a metal oxide semiconductor, other types of gas sensors may be employed, e.g. catalytic sensors or electrochemical sensors.

The displacement of the gas into the interior of the chamber is preferably effected by cyclically varied heating of the interior of the chamber to cause gas expansion and contraction in the chamber and thereby to successively expel the gas residue from the chamber and to draw in fresh gas from the exterior. Alternatively, a mechanical pump arrangement could, for example, be provided for that purpose.

The sensing element in the chamber, in the preferred embodiment of the invention, provides the output signal to associated monitoring equipment, and this signal indicates the presence of detectable gas within the chamber as a function of time. The monitoring equipment analyzes the signal and then indicates the concentration of the detectable gas in the environment.

Prior art gas sensors rely on normal air flow or diffusion to drive the air exchange between the sensor element and the environment. For a given concentration of detectable gas around the sensor, an essentially constant sensor signal results. This type of signal is often referred to as a d.c. signal, and gas detectors utilizing such a signal are said to be operating in a d.c. mode. The term "d.c. mode" refers also to the technique of keeping the sensor operating parameters constant. Unfortunately, environmental conditions such as humidity and temperature can cause the sensor signal to change and, in so doing, induce an erroneous reading of the interpreted concentration of the sensed gas. The level of the sensor signal in any given environmental condition with the concentration of the sensed gas being zero is referred to as a "baseline reading".

Many of the sensing elements mentioned above are incapable of providing any information related to the specific gas being sensed and are often called "wide band" or "non-selective".

In contrast, gas sensing devices embodying the present invention, which for convenience may be referred to as breathing sensors, can reduce environmentally caused errors and provide the following additional benefits:

a. Improved accuracy through the generation of a "baseline reading".

b. Improved accuracy through pre-conditioning of gas samples.

c. Improved selectivity using a technique of "selective consumption" (see below).

d. Improved safety in view of the reduced interference with the environment.

e. Wide range of application by allowing the utilization of a variety of sensing elements.

The method of generating a baseline reading in the sampling chamber consists of removing the sensed gas from the chamber through the use of a consumptive sensor (i.e. a catalytic sensor that is capable of consuming the gas during the measuring process) or through the use of a catalyzer specific to the test gas.

If a breathing gas sensor utilizes a sensing element which actually consumes the detected gases, then a baseline measurement can be taken at the end of every breathing cycle, just prior to exhausting the air out of the sample chamber. The only stipulation for this baseline generation is that the sampled air be kept in the sensing chamber long enough for the sensor to remove virtually all of the detectable gases from the chamber.

If, however, a breathing sensor utilizes a non-consumptive sensing element, a baseline measurement can still be made. This is achieved by introducing a consumptive element into the sample chamber and thereby selectively removing the detectable gases from the chamber.

The consumptive element can also be introduced into a separate pre-conditioning chamber, which would prepare a sample for baseline generation prior to its introduction to the sensing element in the sample chamber.

A sensor embodying the present invention may utilize other chambers in addition to the sampling chamber in order to prepare the air sample for exposure to the sensing element. Specialized filters such as humidity barriers and other semi-permeable membranes can be used to remove undesirable or damaging components from the air as a means of attaining higher accuracy and improved reliability. Thus, environmental air can be diffused into or pumped into the conditioning chamber, and once conditioned, the air sample can then be pumped into the sample chamber.

In one embodiment of the invention several conditioning chambers are used in a parallel arrangement in conjunction with a flow channel multiplexer switch which selects one of the conditioning chambers as the source for the sample chamber. In this manner, several specialized conditioning operations can be carried out consecutively and the specially conditioned air from each of the conditioning chambers can be analyzed separately by the single sensing element. Elaborate measurements can thus be made on environmental air with a relatively simple sensor.

Specialized conditioning of the sample air can be performed in the sample chamber itself. In this case, however, the time sequence of conditioning must be well known in order to ensure that the required measurements are taken at the correct time. As an example, humidity absorbing crystals can be placed between the sensing element and the gas flow permitting means in the sampling chamber. When an intake cycle occurs, these crystals remove a portion of the water vapour from the relatively cool incoming air sample. The sensing element then provides a signal which is relatively independent of humidity, and when the exhaust heater is energized, the hot air flowing past the crystals causes these crystals to give up their trapped water to the hot air, leaving them ready for the next intake cycle.

In addition, drawing sampled air at some unknown temperature into a warm or even hot sampling chamber conditions the air sample to some degree by heating it up towards a standard temperature. This temperature conditioning serves to decrease the dependence of the sensor reading upon the environmental temperature.

When a consumptive sensing element is used in a breathing sensor, and that sensing element consumes only a specific gas or group of gases, then the signal induced in the sensing element due strictly to that gas or group of gases can be differentiated from the signal induced in the sensing element by any and all other environmental factors present in the air sample. This is accomplished by noting the signal just after the introduction of the air sample into the chamber, and then again after the sensor has been given sufficient time to remove all of the consumable gases from the chamber.

Additionally, if the consumptive sensing element can have its consumption properties altered in terms of consumption rates for specific gases or groups of gases by varying one or more of its operating parameters, such as the temperature of the sensing element, then that sensing element can be made to remove several different gases or groups of gases in controlled succession, and the differential signal due to each of these gases or gas groups can be noted. In this manner, a single sensing element gives qualitative and quantitative information about the concentration of several different gases or groups of gases in the chamber.

If a non-consumptive or a very low consumption sensing element is used in a breathing sensor, and if these sensing elements respond to several gases or groups of gases, then quantitative and qualitative information about each of the detectable gas groups present in the sample chamber can be obtained by introducing a selectively variable catalytic device or several selective non-variable catalytic devices into the sample chamber. After an initial overall reading is taken by the sensing element subsequent to a fresh sample of air being introduced into the chamber, the catalyzing element or elements can be operated in a manner so as to sequentially remove each of the catalytically distinguishable gases or groups of gases from the chamber, and in so doing provide a differential signal for each of the distinguishable gases or groups of gases in the sample chamber.

Another advantage of a sensor embodying the present invention is its enhanced safety resulting from the very restricted air flow between the interior of the sensing chamber and the environment, thus reducing the risk of a flame or explosion that could be caused by the sensing element.

Most of the catalytic sensing elements and some of the oxide semiconductor devices in use today must operate at high temperatures to detect the more stable combustible gases such as methane and propane. In environments where high levels of combustible gases can exist, the hot sensor can actually ignite the air and perhaps cause an explosion. Some high temperature catalytic sensors, such as the tin oxide sensors, come equipped with anti-explosion screens to reduce the possibility of an accident, but these screens must not be so restrictive that environmental air does not have easy access to the sensing element. A sensor embodying the present invention however, can isolate the energized sensing element from the environment, and so the probability of an explosion is greatly reduced.

The concept according to the present invention of "breathing gas sensors" can be implemented using any sensing element and the above advantages can be matched to the specific "sensing technology" employed by the sensor. For instance, in the case of a room temperature catalytic sensor, the operational temperature range of the sensor can be expanded to a lower temperature by the use of an embodiment of the present invention which includes a pre-conditioning chamber and in the case of an optical device the preconditioning chamber can be utilized for better shielding from ambient light interference etc.

BRIEF DESCRIPTION OF THE DRAWINGS

The invention will be more readily understood from the following description, given by way of example only, of preferred embodiments thereof when taken in conjunction with the accompanying drawings, in which:

FIGS. 2 and 4 show a block diagram of the electrical system of the sensor of FIG. 3;

FIGS. 5, 6 and 7 show graphs illustrating the operating characteristics of the sensors of FIGS. 1 and 2 and of a third type of sensor;

FIG. 8 shows a view in cross-section through a third embodiment of the invention; and FIG. 9 shows a view in cross-section through a fourth embodiment of the invention.

DESCRIPTION OF THE PREFERRED EMBODIMENT

Figure 1:
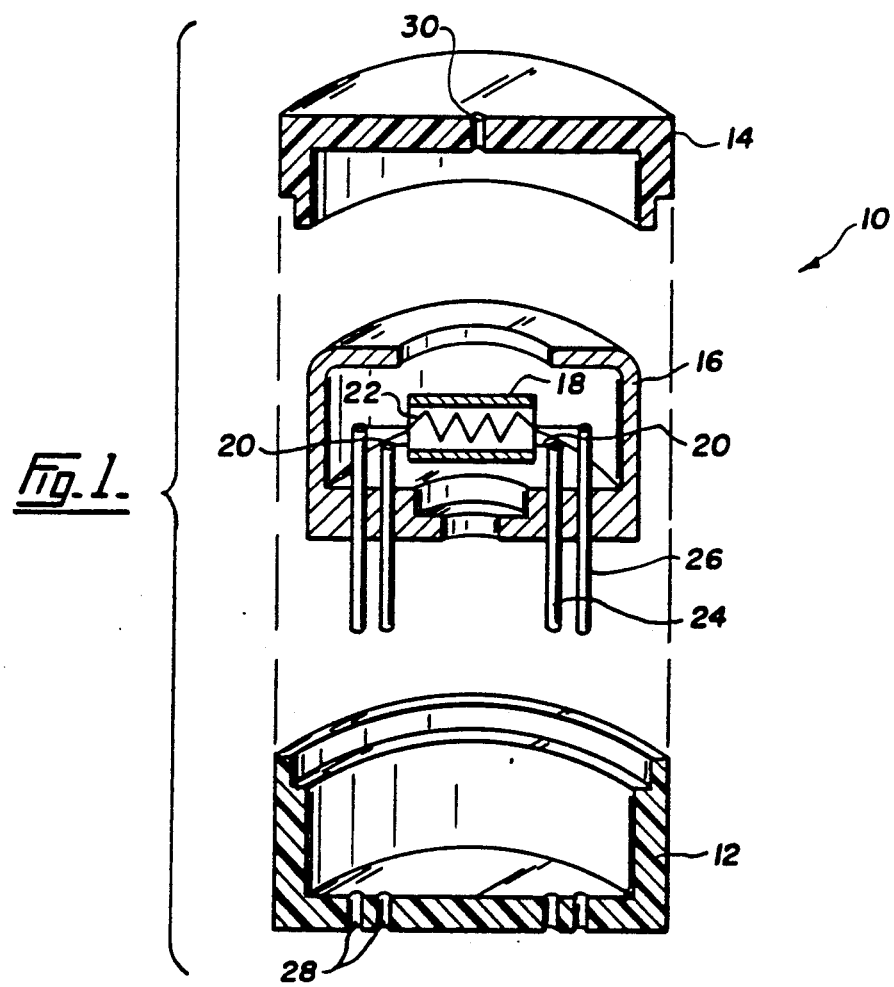
FIG. 1 shows a diagrammatic exploded view in perspective of a gas sensor according to a first embodiment of the invention.

Referring now to FIG. 1 of the accompanying drawings, there is illustrated therein a gas sensor indicated generally by reference numeral 10 which is contained in a housing which comprises a lower housing part 12 which mates with an upper housing part 14, a sealant (not shown) being provided between these parts to seal them together in an airtight manner.

The lower and upper housing parts 12 and 14 are of plastic material and receive within them an inner housing part 16, also of plastic material.

A cylindrical gas sensing element 18 is mounted within the housing 16 and is connected to a pair of electrodes 20, which serve to connect a DC output signal from the sensing element 18 to the electrical system of the gas sensor, as described in greater detail below.

In addition, the cylindrical sensing element 18 contains therein a heating element 22 which, as described in greater detail below, serves the dual purposes of heating the sensing element 18 and also heating the gas in the interior of the housing.

The electrodes 20 and heating element 22 are connected to pins 24 and 26, which project through holes 28 in the bottom of the lower housing part 12.

The upper housing part 14 is formed in its top with a central orifice 30, through which a sample of gas is drawn into the interior of the sampling chamber defined by the housing parts 12 and 14.

The sensing element 18 and its associated electrodes 20 the heating element 22 and the inner housing part 16 are conventional components of a metal oxide semi-conductor gas sensor.

In the present gas sensor, however, the sensing element 18 is not exposed to the ambient atmosphere, but can communicate with the environment at the exterior of the sampling chamber only through the orifice 30.

In addition, the heating element 22 is employed not only to perform its conventional function of heating the sensing element 18, but also generate sufficient thermal energy, when energized cyclically, to cause successive cycles of expansion and contraction of the gas within the sampling chamber and, thus, to cause fresh samples of gas to be drawn in succession through the orifice 30 into the interior of the sampling chamber from the external atmosphere for sensing by the sensing element 18 and then to cause expulsion through the orifice of at least a portion of the residue of the gas samples.

Thus, the gas sensor device performs a "breathing" action. When the heater 22 is energized, the gas sensing device exhales, and when the energization of the heating element 22 is interrupted or reduced, the gas sensing device inhales from the environment. Very little diffusion between the interior of the sensor housing and the environment occurs after the first seconds of inhalation and exhalation and, thus, the device performs a very simple "sampling" of the environment. The sensing element 18, which is of tin oxide with the addition of a small amount of a catalyst (i.e. palladium) in the present embodiment, consumes detectable gas at a rate sufficient to use up most of this gas in the sample chamber over a relatively short cycle time. The gas thus inhaled into the sampling chamber is quickly reduced to reproducible conditions of temperature and humidity and thus the sensing of the gas is less affected by these parameters than in the case of prior devices. Also, the exchange of gas with the environment occurs through the orifice 30, which has microscopic dimensions consistent with the prevention of flame propagation, permitting intrinsically safe application of the gas sensor.

While in the present embodiment of the invention the gas sensing element 18 is a semi-conducting element, various other commercially available devices could alternatively be employed, for example a simple catalytic element such as a platinum wire.

The heating element 22 is switched between two power levels, i.e. a low and a high power level, in an accurately cycled manner, the low level of power being applied to the heater for a fixed time T1 (FIG. 5) and the high level of power being applied for a fixed time T2.

Figure 2:
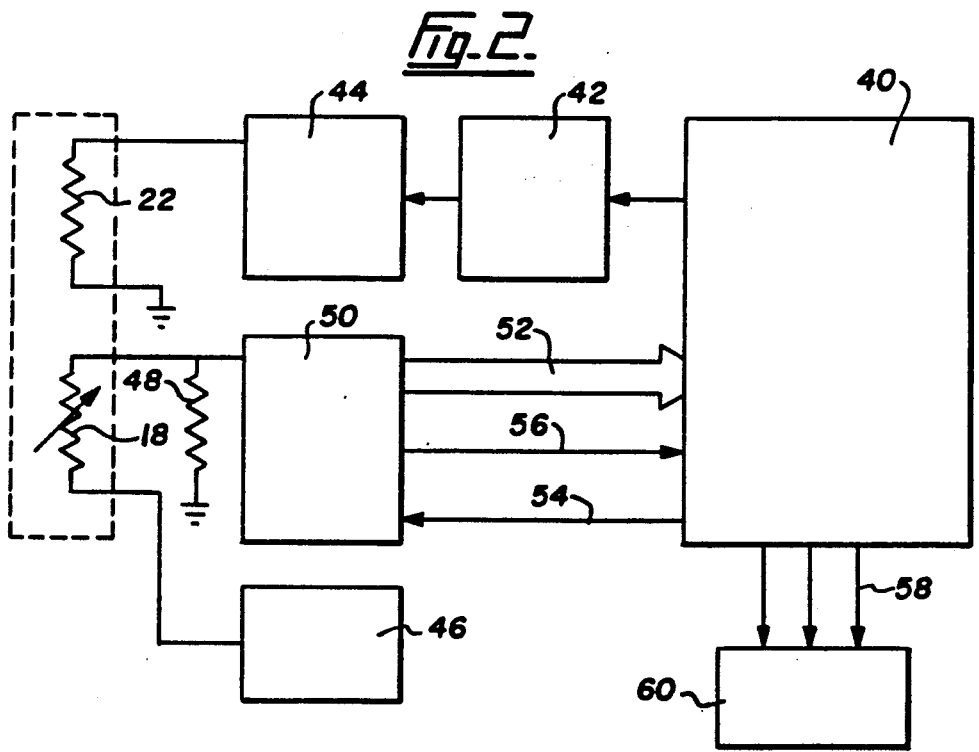
FIG. 2 shows a block diagram of the electrical system of the sensor of FIG. 1.

The electrical system of the gas sensor of FIG. 1 is shown in FIG. 2. The sensor heater element 22 is cycled by a timer implemented by the microcontroller 40. The microcontroller 40 controls the switching operation of a heater control circuit 42. The heater control circuit 42 selects between two pre-set voltage levels, and these voltage levels are fed to a heater driver circuit 44 which is capable of supplying the power to the gas sensor heating element 22 at the above-mentioned low and high power levels as specified by the heater control circuit voltage level.

A voltage regulator 46 provides the tin oxide sensing element with a constant voltage. The element 18 is connected in series with a sensor load resistor 48 which is used to monitor the variable resistance of the sensing element 18. An analog to digital converter 50 with sufficient resolution converts the voltage across the load resistor into digital values. These values are then loaded into the microcontroller 40 through the data bus 52. The conversion process is controlled by the microcontroller 40 through convert control line 54, and the analog to digital converter loads the converted load resistor voltages into the microcontroller 40 by controlling data latch line 56. The microncontroller 40 then analyzes this data to determine the concentration of the target gas, and activates alarm control lines 58, as required, to operate an alarm device 60.

During the period T2, the sensing element 18 detects the presence of combustible gases in the upper chamber and, in doing so, consumes such gases. The thermal energy from the heating element 22 causes the air in the chamber to expand continuously in the time T2 and to escape through the orifice 30.

Since the orifice 30 restricts the air flow, the flow of gas during the time T2 is almost totally out of the chamber. At the end of the time T2, only a fraction of the original air sample remains in the sampling chamber, and this air will have most of its detectable gas component removed through catalyzation.

At the beginning of the time T1, the air left in the chamber begins to cool and contract, and consequently a new sample of air flows into the sample chamber.

By the end of the time T1, the intake cycle is complete and the overall cycle begins again.

During the time T2, the sensor signal will change with time in a manner corresponding to the amount of detectable gases in the sample. The output signal of the sensing element 18 can be analyzed to determine the concentration of detectable gases in the chamber, which will be a good indication of the concentration of detectable gases in the environment.

If the time T2 is of sufficient length, then the signal at the end of time T2 will provide a baseline measurement which is approximately independent of the concentration of detectable gas in the environment.

If the consumptive sensing element displays selective catalysis that can be controlled by varying one of its operating parameters, then the cycle can be easily modified to endow the sensor with discrimination capabilities. In the case of a metal oxide sensor, the controlling parameter is the temperature, and the heater voltage in turn controls that of the sensing element temperature. In this situation, the heater voltage during time T1 can, for example, be set so that the sensing element will detect incoming alcohols and ketones but ignore the hydrocarbons. Because of this, the sensing element will produce a signal during time T1 which indicates the presence of alcohols and ketones and this element will consume some or all of these gases, and the signal during time T2 will largely reflect the presence of hydrocarbons. In the case of propane detectors, alcohols and ketones represent "noise gases" which will cause a false alarm in a conventional tin oxide sensor operated in a d.c. mode, whereas the present tin oxide device with discriminating capabilities will alarm only in the presence of propane or another hydrocarbon.

The discrimination capability can be further improved by using more than two heater levels over the course of a cycle. The number of levels used and the value of the levels themselves are application oriented, and are determined through experimentation.

If, in another embodiment of the invention, a sensing element which does not generate appreciable heat is to be used in a breathing sensor, or if it is desirable to control the pumping action separately from the thermal operation of the heat generating sensing element, then an independent heating element can be introduced into the sample chamber to drive the pumping action.

Figure 3:
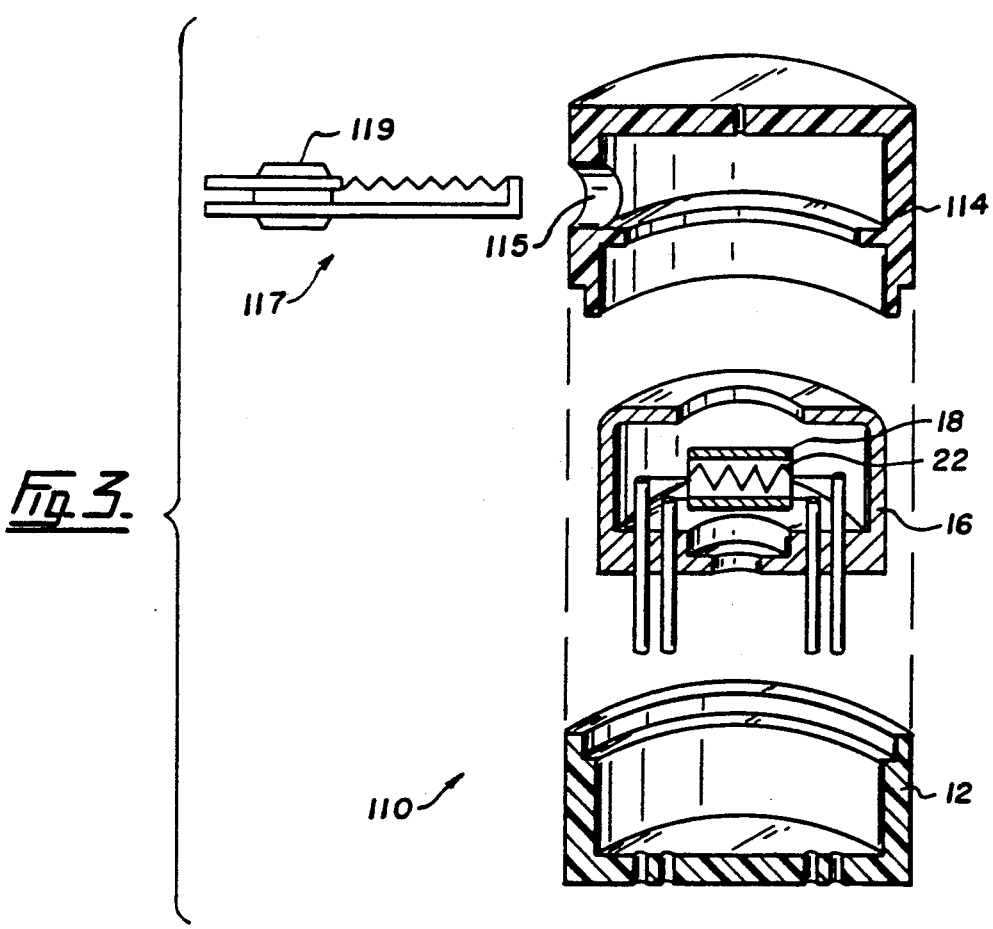
FIG. 3 shows a view corresponding to FIG. 1 but of a second embodiment of the invention.

As shown in FIG. 3, in which the same reference numerals have been employed as in FIG. 1 to indicate parts which correspond to those of the gas sensor of FIG. 1, a gas sensor indicated generally by reference numeral 110 comprises a housing with a lower part 12 similar to that of FIG. 1, but with an upper housing part 114 which is different from the housing part 14 of FIG. 1 in that the housing part 114 is formed with a lateral opening 115.

This opening 115 serves to receive an auxiliary heater, indicated generally by reference numeral 117, which is inserted into the housing for heating the air in the interior of the sample chamber and which, thus, is separate from the sensor comprising the sensing element 18 and the heating element 22 extending through the interior of the sensing element 18.

The auxiliary heating element 117 is provided with a plug 119 which, on insertion of the auxiliary heating element 117 into the housing, plugs and thereby closes the opening 115 so as to prevent the passage of air into and from the sampling chamber through the opening 115.

Figure 4:
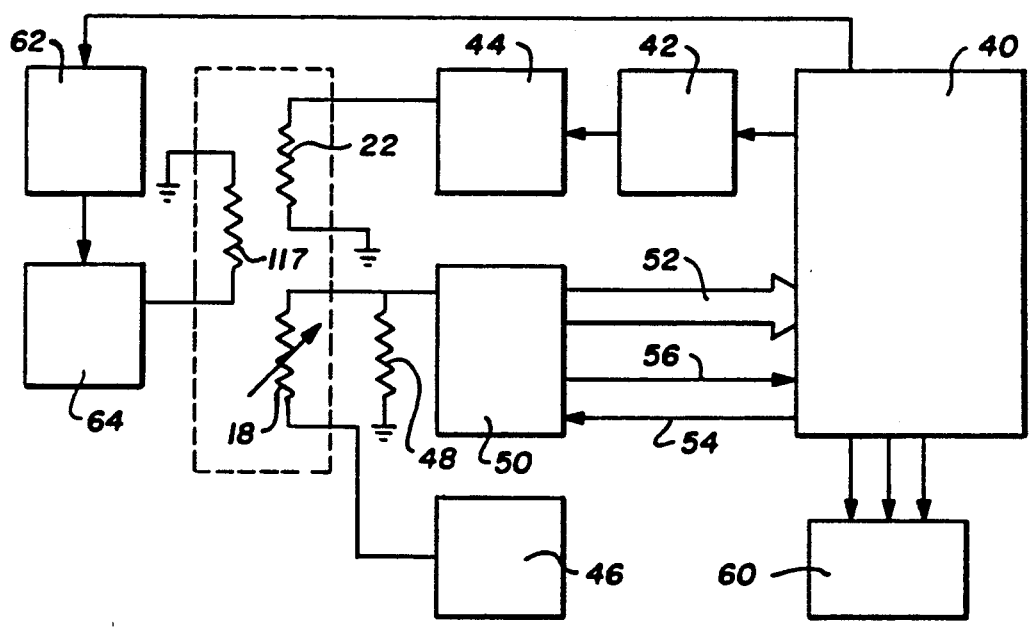

The electrical system of the gas sensor of FIG. 3 is illustrated in FIG. 4, in which components similar to those of FIG. 2 are indicated by the same reference numerals.

In this case, however, the auxiliary heating element 117, serving as an independent thermal pump, is cycled by a timing function generated by the microcontroller 40. The microcontroller 40 then feeds a control signal to a thermal pump controller 62. The controller 62 selects between several pre-set voltages and then feeds the selected voltage to a pump driver 64 which is capable of supplying the power to the independent thermal pump or auxiliary heating element 117 as specified by the pump controller voltage.

Typical responses of breathing gas sensors such as described above are shown in FIGS. 5 through 7.

FIG. 5 represents the response of the self pumped breathing sensor of FIG. 1 and was obtained using clean air, propane and isopropyl alcohol at different concentrations, as indicated. As can be seen, when the voltage H of heating element 22 goes high, the sensor signals illustrated by curve A, obtained from the sensing element 18 when testing clean air, increases to a constant value, as a result of heating of the sensing element. The curves B-E, however, increase initially to a peak level as the sensor element is heated and then fall to a constant level as the sensor stabilizes and the gas is consumed. When the heater voltage H goes low, all of the curves A-E fall from their constant values, as the sensing element 18 cools and a fresh sample of gas is inhaled through the orifice 30. Various algorithms can be used to extract information relating to both the concentration and identification of the gas through numerical analysis of the data.

FIG. 6 shows a similarly obtained response from the independently pumped breathing gas sensor of FIG. 3. In this case, the temperature of the sensing element 18 varies only slightly, causing a correspondingly slight variation in the clean air curve A, while the pumping is effected by the auxiliary heating element 117. However, the curves B1 and C1 illustrate that, during the first half of each cycle, the pump voltage P1 of the auxiliary heating element goes high, while the gas under test expands and is thereby exhaled, causing the sensor signal to fall. In the second half of the cycle, the pump voltage P1 goes low, a fresh sample of gas is inhaled and this causes the sensor response, represented by the curves B1 and C1, to increase initially to a peak. The sensor voltage then decreases as the gas is consumed by the sensing element 18.

Finally, FIG. 7 illustrates the type of responses that can be obtained using the method of selective discrimination using a platinum heater for breathing purposes and varying the temperature of the semiconductor sensor to achieve different rates of consumption for different gas species. In this case the most useful information can be obtained through an analysis of the reaction rate at the end of each temperature step. Thus, in FIG. 7, which is provided as an illustration of an experiment to investigate the use of the sensor of FIG. 3 in greater detail, the line P2 illustrates the cyclical energization of the auxiliary heater 117, while the line H2 illustrates the simultaneous cycling of the energization of the sensor element heater 22. As can be seen, the voltage of the heater 22 is reduced in steps. Curve A2 shows the sensor voltage using clean air, curves B2 and C2 are corresponding curves showing concentrations of 500 ppm and 1000 ppm, respectively, of propane, and curve D2 is the corresponding curve for a mixture of 1000 ppm propane and 480 ppm acetone.

During the initial energization of the auxiliary heater 117, from 0 to about 3 seconds, the air or gas sample is exhaled, and by varying the heater voltage H2 stepwise as shown, the effect of the sensor heater temperature can be seen from the curves, which fall as voltage H2 is reduced and which then rise again, upon reenergization of the heater 22 at about 33 seconds, when the curves B2, C2 and D2 rise to peaks and then fall to substantially constant values as the sensor temperature stabilizes.

When the heater 117 is reenergized at 65 seconds, a fresh gas sample is inhaled and the curves B2, C2 and D2 again rise to peaks and then fall, as shown, as the heater voltage H2 is again reduced in a stepped fashion.

Thus, the curves between 3 and 65 seconds represent the effect on the sensor voltage of the sensor temperature variations alone, after most of the gases have been exhaled whereas the curves between 65 and 100 seconds represent the sensor voltage variation after inhalation of a new gas sample. By comparing these results, the presence of either propane or acetone can be detected.

Depending on the specific requirements of a user, it is possible to construct an algorithm to achieve the required analytical results with improved accuracy within the capability of the sensing element used in the sensor.

For example, the sample gas could be passed through one or more conditioning chambers to the sampling chamber.

In some cases, a heated catalytic element can be used to provide for removal of certain gases for baseline generation as well as to provide the pumping action for the chamber.

Also the use of a mechanical pump to supply the sample chamber with air can be employed to remove the effects of having a change in sample temperature associated with the pumping cycle. This can prove advantageous for certain applications of breathing sensors which incorporate highly temperature sensitive gas sensing elements. In addition, the amount of air volume moved over the course of a sample cycle and the rate at which it is moved can be very easily controlled.

Many methods of mechanical pumping are available, and any one of these methods could be used to realize a breathing sensor. Examples of these methods include solenoid pumps, rotating motor driven pumps, and piezo-electrically driven pumps.

For example, in FIG. 8 of the accompanying drawings there is shown one embodiment of the present invention which employs mechanical pumping for supplying gas from the ambient atmosphere to a gas sensing element.

More particularly, the apparatus illustrated in FIG. 8 comprises a cylindrical housing 200, which is formed with orifices 202 and 204 at opposite ends of the housing 200. The orifices 202 and 204 are provided with reed valves 206 and 208, respectively, which are provided at the interior of the housing 200 and the exterior of the housing 200, respectively. Thus, the valve 206 serves to permit the entry of gas into the sampling chamber formed by the interior of the housing 200, while the valve 208 serves to permit the outflow of gas from this sampling chamber to the exterior of the housing 200 through the orifice 204.

The gas sensing element in this embodiment is indicated by reference numeral 210 and is located in the sampling chamber within the housing 200.

The housing 200 is provided with an auxiliary housing 212 for containing a diaphragm pump 214, which extends across an opening 216 in one side of the auxiliary housing 212.

An orifice 218 in the opposite side of the housing 212 is provided with a reed valve 220, located in the interior of the auxiliary housing 212, for preventing the outflow of gas to the environment through the orifice 218 while allowing the inflow of gas into the auxiliary chamber 212 through the orifice 218 in response to operation of the diaphragm pump 214.

The operation of the diaphragm pump 214 is effected by a pump driver circuit 222.

In operation of this embodiment, the pumping action of the diaphragm pump 214 draws gas from the surrounding atmosphere into the auxiliary housing 212 through the orifice 218 and then expels this gas from the auxiliary housing 212 through the orifice 202 into the sampling chamber within the housing 200 for sensing by the gas sensing element 210. After its been sensed, the residue of this gas is expelled through the orifice 204 to the surrounding atmosphere.

As will be apparent from the above description of the embodiments of FIGS. 1 and 3, a simple pneumatically restrictive element such as the orifice 30 can be used to allow movement of air into and out of the chamber yet still isolate the chamber. Diffusion driven air exchange through the orifice can be controlled by such parameters as the size of the orifice and the pressure differential between the chamber and the environment. A slow but consistent flow of sample air out of the chamber due to a pressure differential between the chamber and the environment can be achieved by constant heating of the air sample in the chamber during the sample period.

On the other hand, simple flap valves or springed valves controlled strictly by the pressure differential across them can be used, as in the embodiment of FIG. 8, to regulate the direction of flow of air into and out of the sampling chamber.

More precise control of air movement into and out of the sampling chamber can be achieved through the use of actively controlled valves. For example, a valve controlled by a piezo-electric element could be opened or closed at will to guarantee precise timing of the breathing cycle. In addition, an actively controlled valve would allow a pressure difference to exist between the sampling chamber and the environment.

Several chambers could be connected in series to deliver specialized performance characteristics. These chambers could be any combination of conditioning and sampling chambers. A single pumping element or several pumping elements could be used to control the air flow through the system. The chambers could be isolated from each other by any combination of pneumatically restrictive elements.

Specialized performance characteristics of a breathing sensor could also be obtained by connecting various combinations of specialized sampling and conditioning chambers in a parallel manner, with various pumping and valving elements controlling the interaction of the individual chambers. In fact, any combination of series and/or parallel elements could be used to create specialized networks of conditioning and sensing elements to perform specific gas sensing tasks.

FIG. 9 shows yet another embodiment of the invention, in which there is provided a single conditioning chamber into which gas is drawn form the environment so as to be conditioned before being fed from the conditioning chamber into the sampling chamber.

More particularly, in this embodiment there is provided an elongate cylindrical housing 300 having opposite end walls 302 and 304, the interior of the housing 300 being divided by an intermediate partition wall 306 into a conditioning chamber 308 and a sampling chamber 310.

An orifice 312 is provided in the end wall 302 to allow the entry of gas from the environment into the conditioning chamber 308. A heating element 314 is provided within the conditioning chamber 308 for heating the gas in the conditioning chamber 308.

The partition wall 306 is formed with an orifice 316, provided with an air flow control valve 317 located within the sampling chamber 310 so as to allow the entry of gas into the sampling chamber 310 through the orifice 316 from the conditioning chamber 308 but to prevent the outflow of gas from the sampling chamber 310 through the orifice 316 into the conditioning chamber 308.

The cylindrical wall of the housing 300 is also formed with an outlet orifice 318, provided with an exhaust flow valve 320 at the exterior of the housing 300 for allowing gas to escape from the sampling chamber 310 to the environment through the orifice 318.

The sampling chamber 310 contains a semiconductor gas sensing element 322, such as that employed in FIG. 1. In addition, a heating element 324 is provided within the sampling chamber 310 to serve as a thermal pump, similar to the heating element 117 of FIG. 3.

In operation of this embodiment, the heating element 324 is alternately energized and de-energized so as to effect successive cycles of expansion and contraction of gas in the sampling chamber 310.

The contraction of the gas in the sampling chamber 310 causes fresh gas to be drawn into the sampling chamber 310 from the conditioning chamber 308, whereas the expansion of gas within the sampling chamber 310 causes gas residue to be expelled through the orifice 318, following sensing of the gas by the gas sensor 322.

Before the gas flows through the orifice 316 from the conditioning chamber 308 into the sampling chamber 310, it is heated, as required, by the heating element 314 to control the temperature of this gas, e.g. for the purpose of maintaining a constant predetermined temperature of the gas flowing into the sampling chamber 310.

In other embodiment of the invention, which are not shown in the drawings, a plurality of chambers are connected in series to deliver specialized performance characteristics. These chambers are in various combinations of conditioning and sampling chambers. A single pumping element or several pumping elements is/are used to control the air flow through the chamber, which can be isolated from each other by any combination of pneumatically restrictive elements.

Specialized performance characteristics of a breathing sensor could also be obtained by connecting various combinations of specialized sampling and conditioning chambers in a parallel manner, with various pumping and valving elements controlling the interaction of the individual chambers. In fact, any combination of series and/or parallel elements could be used to create specialized networks of conditioning and sensing elements to perform specific gas sensing tasks.

We claim:

1. A gas sensing device comprising:
   means defining a sampling chamber for containing a gas to be sensed by said sensing device;
   a gas sensing element within said chamber for providing an output signal which varies in response to the presence of said gas in said chamber;
   means for permitting restricted gas flow between the interior and the exterior of said chamber;
   means for displacing a sample of the gas through said gas flow permitting means into the interior of said chamber for sensing by said sensing element and for subsequently displacing gas from the interior to the exterior of said chamber; and
   means for cyclically operating said displacing means to thereby repeatedly draw the gas into said chamber and expel gas from said chamber in succession.

2. A gas sensing device as claimed in claim 1, wherein said displacing means comprise means for heating the interior of said chamber, said means for cyclically operating comprising means for effecting cyclically varying energization of said heating means.

3. A gas sensing device as claimed in claim 2, wherein said heating means comprise electrical heating element means provided within said chamber for heating said sensing element to produce said output signal.

4. A gas sensing device as claimed in claim 2, wherein said sensing element comprises a metal oxide sensing element forming part of a semiconductor gas sensor, and said heating means comprise a heating element of said semiconductor gas sensor.

5. A gas sensing device as claimed in claim 2, wherein said sensing element forms part of a gas sensor provided within said chamber and said heating means comprises a heating element also provided within said chamber, said heating element being separate from said gas sensor.

6. A gas sensing device as claimed in claim 1, therein said gas flow permitting means comprise an orifice in the wall of said chamber.

7. A gas sensing device as claimed in claim 2, further comprising means defining an additional chamber communicating with said sampling chamber, said displacing means comprising means for displacing the gas sample from said additional chamber to said sampling chamber, and means in said additional chamber for conditioning said gas sample.

* * * * *